(12) United States Patent
Pento et al.

(10) Patent No.: US 7,960,548 B2
(45) Date of Patent: Jun. 14, 2011

(54) KERATINOCYTE GROWTH FACTOR RECEPTOR—TYROSINE SPECIFIC INHIBITORS FOR THE PREVENTION OF CANCER METASTATIS

(75) Inventors: J. Thomas Pento, Norman, OK (US); Pui-Kai Li, Galloway, OH (US); Robert W. Brueggemeier, Dublin, OH (US); John C. Hackett, Dublin, OH (US)

(73) Assignees: The Ohio State University Research Foundation, Columbus, OH (US); The Board of Regents of the University of Oklahoma, Norman, OK (US)

( * ) Notice: Subject to any disclaimer, the term of this patent is extended or adjusted under 35 U.S.C. 154(b) by 90 days.

(21) Appl. No.: 11/414,890

(22) Filed: May 1, 2006

(65) Prior Publication Data

US 2007/0078176 A1 Apr. 5, 2007

Related U.S. Application Data

(60) Provisional application No. 60/676,029, filed on Apr. 29, 2005, provisional application No. 60/687,222, filed on Jun. 3, 2005.

(51) Int. Cl.
*C07D 471/02* (2006.01)
*C07D 215/22* (2006.01)
*C07D 215/227* (2006.01)

(52) U.S. Cl. ............... 546/62; 546/157; 546/158

(58) Field of Classification Search ............. 546/62, 546/157, 158
See application file for complete search history.

(56) References Cited

U.S. PATENT DOCUMENTS

| | | | | |
|---|---|---|---|---|
| 3,330,823 | A * | 7/1967 | Bernstein et al. | 540/461 |
| 5,023,261 | A * | 6/1991 | Kamijo et al. | 514/285 |
| 5,348,962 | A | 9/1994 | Kulagowski et al. | |
| 6,716,880 | B2 | 4/2004 | Li et al. | |
| 6,855,726 | B1 * | 2/2005 | Dudley et al. | 514/312 |

FOREIGN PATENT DOCUMENTS

| | | | |
|---|---|---|---|
| WO | WO 9950263 A1 * | 10/1999 | |
| WO | WO 02051835 A1 * | 7/2002 | |
| WO | WO 03020698 A2 * | 3/2003 | |
| WO | 2006/119148 A2 | 11/2006 | |

OTHER PUBLICATIONS

Kanaoka et al. Tetrahedron Letters 1980, 21(40), 3893-6.*
Kappe et al. Chemische Berichte 1978, 111(12), 3857-66, (CAS Abstract and Structures attached).*
Hubner et al. Berichte der Deutschen Chemischen Gesellschaft 1908, 41, 482-7, (CAS Abstract and structure attached).*
Collington et al. Journal of the Chemical Society C: Organic 1968, 8, 1017-20. The CAS abstract and chemical structure of 3,4-dihydro-3-(2-methoxyphenyl)-1(1H)-quinolinone are provided.*
Wislicenus et al. Annalen der Chemie, Justus Liebigs 1920, 421, 119-58; the CAS abstract and structure are attached.*
Hey et al. Journal of the Chemical Society 1949, 3164-71; the CAS abstract and structure are attached.*
Walser et al. Journal of Heterocyclic Chemistry 1975, 12(2), 351-8; the CAS abstract and structure are attached.*
Xiao et al. Bioorganic & Medicinal Chemistry Letters 2001, 11, 2875-78.*
El Ali et al. J. Am. Chem. Soc. 1996, 118, 4264-4270.*
Uray et al. Helvetica Chemica Acta 1999, 82(9), 1408-1417.*
Li et al. Bioorg. Med. Chem. Lett. 2001, 11, 1687-90.*
Zang, Xiao-Ping, et al., "KGF-induced motility of breast cancer cells is dependent on Grb2 and Erk1,2," Clinical & Experimental Metastasis 21, pp. 437-443, 2004, Kluwer Academic Publishers, Netherlands.
Zang, Xiao-Ping, et al., "Keratinocyte growth factor-induced motiblity of breast cancer cells," Clinical & Experimental Metastasis 18, pp. 573-580, 2001, Kluwer Academic Publishers, Netherlands.
International Search Report mailed Sep. 25, 2007 for WO 2006/119148 A2.
Written Opinion mailed Sep. 25, 2007 for WO 2006/119148 A2.
International Preliminary Report on Patentability issued Oct. 30, 2007 for WO 2006/119148 A2.

* cited by examiner

*Primary Examiner* — Jason M Nolan
(74) *Attorney, Agent, or Firm* — Calfee, Halter & Griswold LLP

(57) ABSTRACT

Compounds and methods for treating, inhibiting, or delaying the onset of cancer in a subject by administering a therapeutically effective amount of a keratinocyte growth factor receptor tyrosine kinase (KGFR TK) inhibitor to the subject in need of such treatment. Also provided are compounds and methods for the treating, inhibiting, or delaying the onset of metastasis in a subject with cancer by administering a therapeutically effective amount of a KGFR TK inhibitor to the subject in need of such treatment.

11 Claims, 9 Drawing Sheets

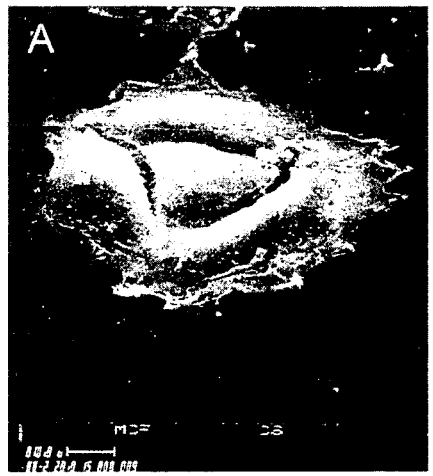
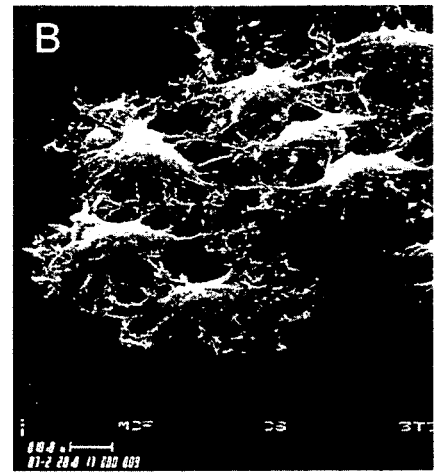
Fig. 1A  Fig. 1B
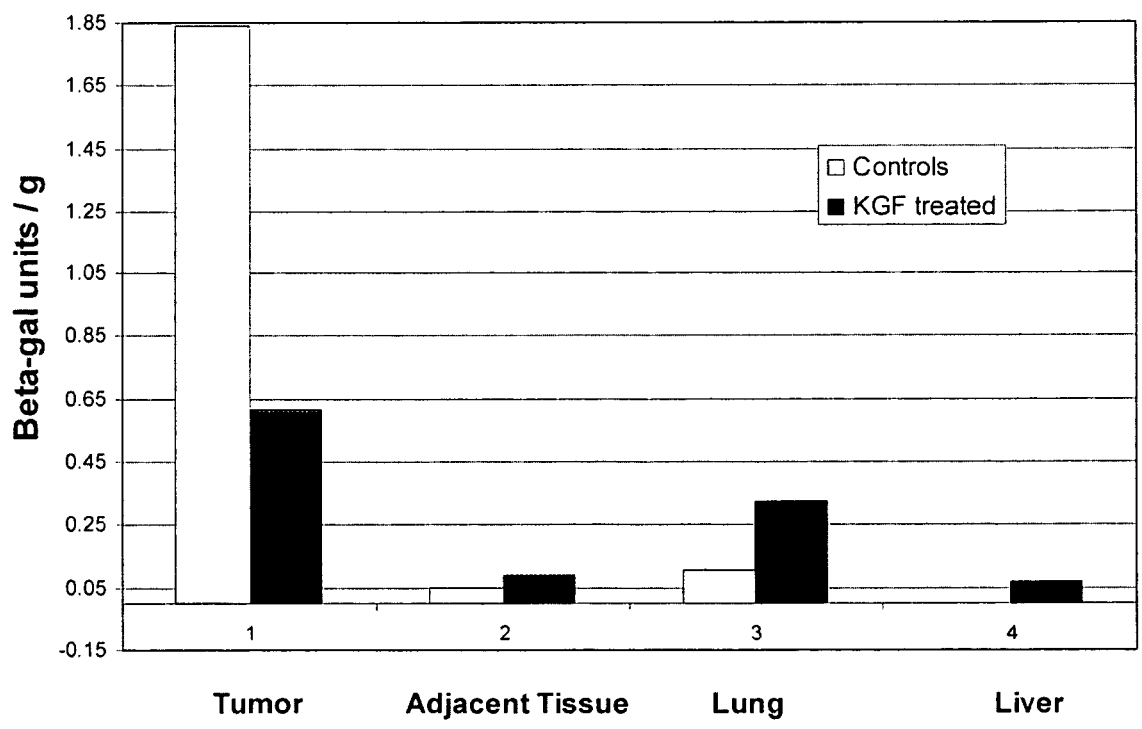
Fig. 2

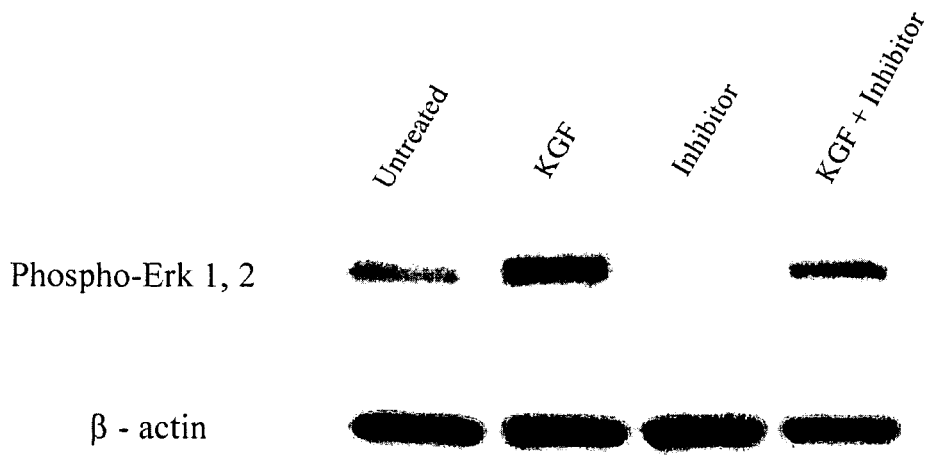

Phospho-Erk 1, 2

β - actin

Fig. 3 hKGFR: 481 LTLGKPLGEGCFGQVVMAEAVGIDKDKPKEAVTVAVKMLKDDATEKDLSDLVSEMEMMKM 540
mKGFR: 481 LTLGKPLGEGCFGQVVMAEAVGIDKDKPKEAVTVAVKMLKDDATEKDLSDLVSEMEMMKM 540
FGFR1: 478 LVLGKPLGEGAFGQVVLAEAIGLDKDKPNRVTKVAVKMLKSDATEKDLSDLISEMEMMKM 537 hKGFR: 541 IGKHKNIINLLGACTQDGPLYVIVEYASKGNLREYLRARRPPGMEYSY*DINRVPEEQMTF* 600
mKGFR: 541 IGKHKNIINLLGACTQDGPLYVIVEYASKGNLREYLRARRPPGMEYSY*DINRVPEEQMTF* 600
FGFR1: 538 IGKHKNIINLLGACTQDGPLYVIVEYASKGNLREYLQARRPPGLEYSYNPSHNPEEQLSS 597 hKGFR: 601 KDLVSCTYQLARGMEYLASQKCIHRDLAARNVLVTENNVMKIADFGLARDINNIDYYKKT 660
mKGFR: 601 KDLVSCTYQLARGMEYLASQKCIHRDLAARNVLVTENNVMKIADFGLARDINNIDYYKKT 660
FGFR1: 598 KDLVSCAYQVARGMEYLASKKCIHRDLAARNVLVTEDNVMKIADFGLARDIHHIDYYKKT 657 hKGFR: 661 TNGRLPVKWMAPEALFDRVYTHQSDVWSFGVLMWEIFTLGGSPYPGIPVEELFKLLKEGH 720
mKGFR: 661 TNGRLPVKWMAPEALFDRVYTHQSDVWSFGVLMWEIFTLGGSPYPGIPVEELFKLLKEGH 720
FGFR1: 658 TNGRLPVKWMAPEALFDRIYTHQSDVWSFGVLLWEIFTLGGSPYPGVPVEELFKLLKEGH 717 hKGFR: 721 RMDKP<u>A</u>NCTNELYMMMRDCWHAVPSQRPTFKQLVEDLDRILTLTTNEE 768
mKGFR: 721 RMDKP<u>T</u>NCTNELYMMMRDCWHAVPSQRPTFKQLVEDLDRILTLTTNEE 768
FGFR1: 718 RMDKP<u>S</u>NCTNELYMMMRDCWHAVPSQRPTFKQLVEDLDRIVALTSNQE 765

Fig. 4

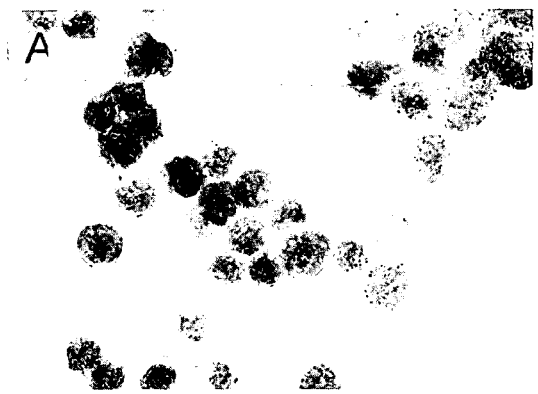 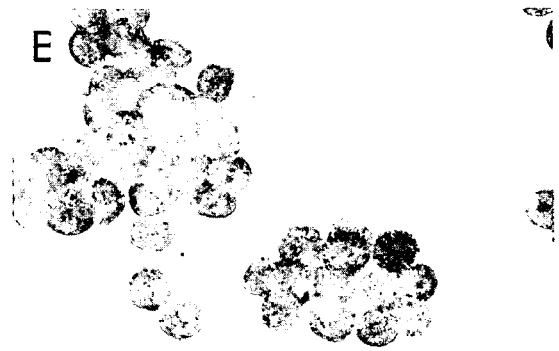
Fig. 10A  Fig. 10B
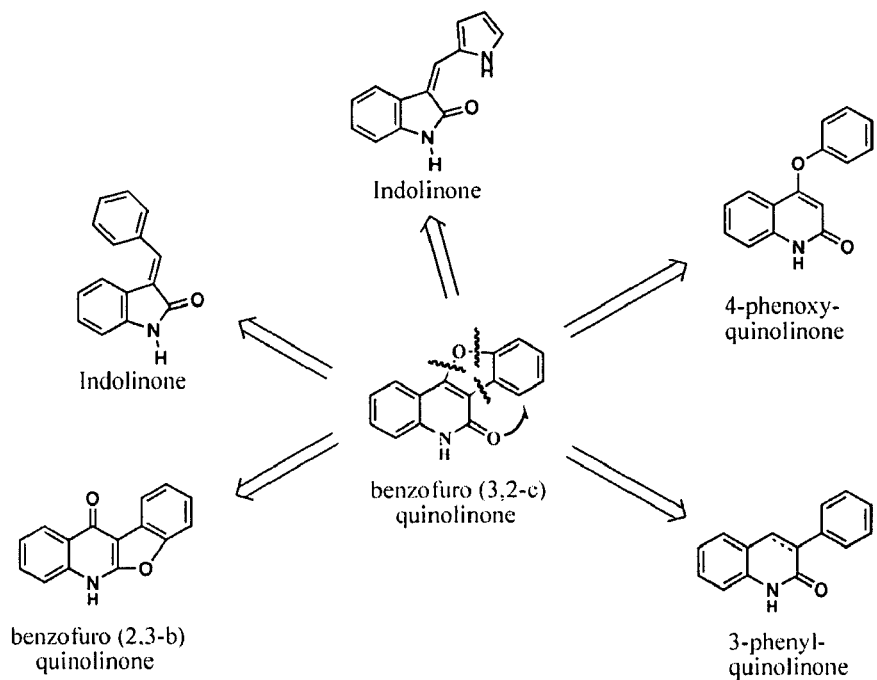
Fig. 11

KERATINOCYTE GROWTH FACTOR RECEPTOR—TYROSINE SPECIFIC INHIBITORS FOR THE PREVENTION OF CANCER METASTATIS

CROSS-REFERENCE TO RELATED APPLICATIONS

This application claims priority to U.S. Provisional Patent Application Ser. No. 60/676,029; filed Apr. 29, 2005 U.S. Provisional Patent Application Ser. No. 60/687,222; filed Jun. 3, 2005. The entirety of each of these applications is incorporated herein by reference.

STATEMENT ON FEDERALLY FUNDED RESEARCH

This invention was supported in part by grants from NIH/NCI (CA-89740 to JT Pento) and DOD (DAMD-170110591 to JT Pento and DAMD-170210459 to AMT). The government may have certain rights in this invention.

BACKGROUND

Current cancer chemotherapy or radiation treatment is designed to kill all rapidly growing cells; thus, resulting in a very high incidence of adverse side effects and toxicity. Further, very few cancer treatments are specifically designed to prevent the metastatic development and progression of cancer. Keratinocyte growth receptor factor-tyrosine specific kinase (KGRF TK) inhibitors would be much less cytotoxic and specifically inhibit a critical step in the metastatic development of cancer cells which is responsible for most of the morbidity and mortality associated with cancer. The KGRF TK antagonists should be highly specific for KGF inhibition and should provide a high level of specificity, efficacy and safety in the treatment and/or prevention of cancer progression and metastasis.

Keratinocyte Growth Factor (KGF) is a member of the fibroblast growth factor family (also designated FGF-7) that is produced in stromal breast tissue and stimulates DNA synthesis, proliferation and migration of epithelial cells in the breast and other tissue (1-3). It is well established that these target epithelial cells contain high affinity KGF receptors (KGFR) (4, 5). In situ hybridization studies confirmed the specific mesenchymal production of KGF and epithelial localization of the KGFR in mammary tissue which provides further evidence that KGF is a mesenchymally-derived mediator of epithelial cell proliferation and migration (6, 7)

The mammary glands of adult female animals are remarkably sensitive to KGF (8). Systemic administration of KGF in adult male and female rats for 3 to 5 days was found to produce massive mammary ductal hyperplasia and an elevation of mitotic figures (8). Accordingly, intraductal hyperplasia is well known to be characteristic of premalignant breast lesions which leads to neoplasia. Similarly, Kitsberg and Leder (9) observed that female mice, with a constitutively up-regulated KGF transgene, develop mammary epithelial hyperplasia and eventually all animals developed metastatic mammary carcinomas. Consistent with this concept, KGFR gene up-regulation was observed in human primary breast tumor specimens (10). However, it was also observed that highly malignant, metastatic breast cancer tissue expressed relatively little KGFR (11). We recently reported that KGF treatment induced an up-regulation of the KGFR gene in ER-positive cells (12). This suggests that KGF-mediated stimulation of breast epithelial proliferation and migration may be an early event in the molecular cascade, which leads to breast cancer progression and metastasis (13). Thus, KGF would be expected to effectively stimulate well differentiated breast cancer cells (e.g. ER-positive breast cancer) and have little or no effect on less differentiated, highly malignant, tumor cells that have escaped normal regulatory mechanisms.

KGF binds to KGFR (also known as FGFR2 IIIb) found in epithelial cells, which is a splice variant of FGFR-2 encoded by the FGFR-2 gene (14). KGFR is a member of the fibroblast growth factor receptor (FGFR) family which are membrane-spanning tyrosine kinase receptors consisting of four known peptides whose sequences are highly conserved (15). It has been shown that there is a transition in the KGFR from the IIIb isoform in primary tumors, which is KGF-responsive, to the IIIc isoform in advanced prostate cancer, which is unresponsive to KGF (16). If this KGFR transition occurs in breast cancer it would also support the concept that KGF is an early signal that is involved in the initiation of the cell migration and progression to aggressive growth and metastasis. Thus, KGF inhibition would provide and opportunity to inhibit breast tumor progression to a malignant phenotype.

Deregulation of receptor tyrosine kinase (TK) activity and the related signal transduction pathways is known to be involved in the development and metastatic progression of breast and other cancers (17). For example, it is well established that over-expression of the EGF receptor is predictive of aggressive and metastatic tumors in breast and other cancers (18, 19). Accordingly, specific TK inhibitors of the EGFR have been found to be effective therapeutically in the treatment of breast and other tumors (20, 21). Since we and other have demonstrated that KGF enhances breast cancer cell migration and tumor progression, we hypothesize that highly specific and potent KGFR TK inhibitors have a significant potential to be highly effective therapeutic agents in the treatment or prevention of breast cancer metastatic progression.

SUMMARY OF THE INVENTION

Provided herein are compounds and methods for the treatment of cancer and cancer metastasis in a subject in need of treatment. The compounds described herein are keratinocyte growth factor receptor tyrosine kinase (KGFR TK) inhibitors.

Provided is a method of treating, inhibiting, or delaying the onset of cancer or cancer metastasis in a subject, the method comprising the step of administering a therapeutically effective amount of a KGFR TK inhibitor to the subject in need of such treatment. In different embodiments, the method may be used in the treatment of several different kinds of cancers, including, but not limited to breast, uterine, ovarian, cervical, colon, rectal, stomach, thyroid, lung, testicular, kidney, bladder, trachea, small intestine, vulva, liver, pancreatic, prostate, and other cancers.

Also provided is a method of treating, inhibiting or delaying the onset of metastasis in a subject having cancer, the method comprising the step of administering a therapeutically effective amount of a KGFR TK inhibitor to the subject in need of such treatment. In different embodiments, the method provided may be used with any of several different cancers, including but not limited to breast, uterine, ovarian, cervical, colon, rectal, stomach, thyroid, lung, testicular, kidney, bladder, trachea, small intestine, vulva, liver, pancreatic, prostate, and other cancers.

The compounds and methods described herein are further useful in combination treatments for cancers, including use in addition to surgery to remove a primary tumor, as well as in conjunction with radiation and/or chemotherapy regimens.

BRIEF DESCRIPTION OF THE DRAWINGS

FIG. 1 shows scanning electron micrographs of control (A) and KGF-treated (B) MCF-7 cells. Micrograph shows cell morphology at 60 minutes post treatment.

FIG. 2 shows the effects of KGF on nude mouse xenografts. In these experiments 5×106 viable MCF-7 cells, transfected with a β-gal reporter plasmid, were embedded into 0.2 ml Matrigel and implanted into female nude mice. Four animal/group were treated with either KGF (2.5 µg/kg) or control vehicle every other day. After 21 days of treatment the tumor, lung and liver tissue were removed and assayed for b-gal activity using a CRPG substrate for β-gal.

FIG. 3 shows Western blots of phospho-Erk1,2 and β-actin from KGF and signaling inhibitor (Grb2 antisense oligo) treated MCF-7 cells. The cells were treated with 50 ng/ml KGF and/or signal transduction inhibitor for 3 days. Equal amounts of protein (10 µg) were loaded for SDS-PAGE analysis.

FIG. 4 shows alignment of human KGFR (hKGFR) (SEQ ID NO: 2), mouse KGFR (mKGFR) (SEQ ID NO: 3) and FGFR-1 (SEQ ID NO: 4) tyrosine kinase domains. Both receptors share 86% amino acid identity with human FGFR-1. Residues not shared between KGFR and FGFR-1 are shown in bold type; residues unshared between the three proteins are underlined and residues unique to KGFR are shown in italics.

FIG. 10 shows immuno-localization of KGFR in MCF-7 cells. These photomicrographs (200×) contain MCF-7 cells that were treated with either vehicle (A) or compound 5 (B) 24 hours before processing for immuocytochemistry. Brown staining represents KGFR localization.

FIG. 11 shows the design of KGFR inhibitors with different structural cores.

DETAILED DESCRIPTION OF THE INVENTION

Figure 5:
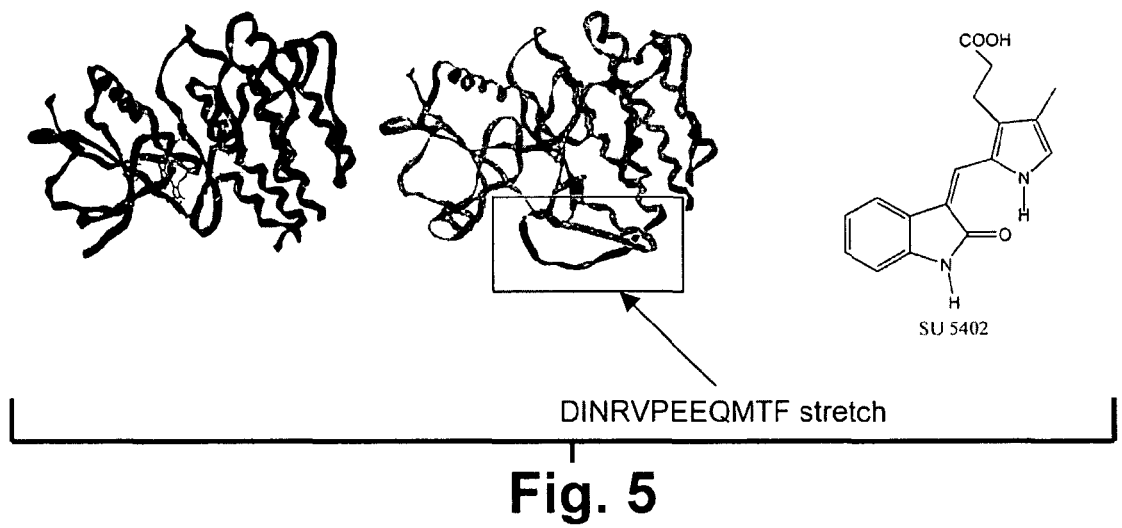
FIG. 5 shows the crystal structure of FGFR-1 (PBD #1FGI) displayed with binding pocket amino acids (left) and SU5402. The KGFR homology model is displayed (right) with the DINRVPEEQMTF (SEQ ID NO: 1) stretch at the bottom of the model shown in the box.

The compounds and methods described herein are useful for the treatment and prevention of metastatic cancer development. The compounds inhibit an early step in the molecular cascade which leads to cancer metastasis. Thus, when a cancer is initially diagnosed, a patient would be treated with a KGFR TK inhibitor to prevent the cancer's metastatic development while the primary tumor is surgically removed or destroyed by radiation and/or chemotherapy. A further application is the prevention of cancer in cancer-free individuals that have a high risk for the development of cancer.

The compounds described herein are not only specific for the inhibition of cancer metastasis, but are also highly specific for an important molecular mechanism involved in the metastatic process. Additionally, the compounds described herein are relatively safe and produce little or no systemic cytotoxicity.

Provided are compounds and methods for treating cancers, specifically metastatic cancers, in subjects in need of such treatment. Provide are compounds of formula I:

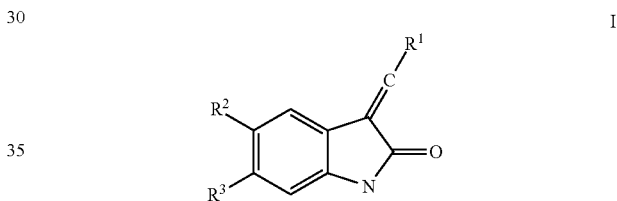

wherein $R^1$ is a substituted aromatic selected, preferably, substituted pyrrolyl or substituted phenyl. The aromatics may have one or more substituents, which are selected from H, alkyl, hydroxyl, carboxylic acid, alkoxy, sulfonamide, and combinations thereof. $R^2$ and $R^3$ may be the same or different and are selected from the group consisting of H, ester, alkoxy, hydroxyl, —OSO$_2$NH$_2$, and combinations thereof. Also included are the pharmaceutically acceptable salts and esters of compound I. In some embodiments, compound 1 is a substituted pyrrolyl having one or more substituents selected from H, C$_1$ to C$_4$ alkyl, C$_1$ to C$_4$ carboxylic acid, and combinations thereof. In other embodiments, compound I is a substituted phenyl having one or more substituents selected from H, hydroxyl, —OSO$_2$NH$_2$, methoxy, ethoxy, propoxy, butoxy, and combinations thereof. In preferred embodiments, compound I is a keratinocyte growth factor receptor-tyrosine specific kinase (KGFR-TK) inhibitor.

Also provided are compounds of formula II:

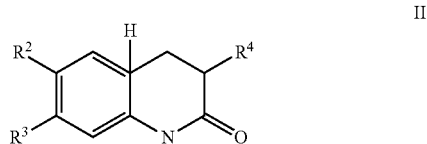

wherein $R^4$ is phenyl and may have one or more substituents selected from H, sulfonamide, hydroxyl, alkoxy, and combinations thereof. $R^2$ and $R^3$ are selected from the group consisting of H, ester, alkoxy, hydroxyl, —$OSO_2NH_2$, and combinations thereof. Also encompassed are the pharmaceutically acceptable salts and esters of compound II. In some embodiments, the phenyl substituent is selected from H, —OH, —$OSO_2NH_2$, methoxy, ethoxy, propoxy, butoxy and combinations thereof. In preferred embodiments, compound II is a keratinocyte growth factor receptor-tyrosine specific kinase (KGFR-TK) inhibitor.

Also provided are compounds of formula III:

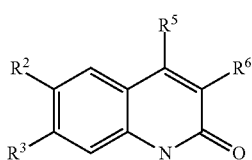

III wherein $R^5$ and $R^6$ are selected from H, phenyl, substituted aromatic, and phenoxy. When $R^5$ or $R^6$ is aromatic, it may have one or more substituents selected from H, alkyl, hydroxy, alkoxy, sulfonamide, $O(CH_2)_nOH$, wherein n is 1-4, and combinations thereof. In some embodiments, $R^5$ and $R^6$ may form a ring. $R^2$ and $R^3$ are selected from H, amino, ester, carboxylic acid, alkoxy, hydroxyl, —$OSO_2NH_2$, and combinations thereof. Also encompassed are the pharmaceutically acceptable salts and esters of compound III.

In some embodiments of compound III, $R^5$ is H and $R^6$ is phenyl or substituted phenyl, wherein the substituted phenyl may have one or more substituents selected from H, hydroxy, methoxy, ethoxy, propoxy, butoxy, —$OSO_2NH_2$, —$O(CH_2)_nOH$, wherein n is 1-4, and combinations thereof. In other embodiments, of compound III, $R^5$ is phenoxy and $R^6$ is H. In still other embodiments, $R^5$ and $R^6$ of compound III form a heteroaryl ring. In some embodiments, this heteraryl ring is fused to another aromatic ring. In a specific embodiment, $R^5$ and $R^6$ form a furyl ring, wherein the furyl ring is fused to a benzene ring. In preferred embodiments of compound III, compound III is a keratinocyte growth factor receptor-tyrosine specific kinase (KGFR-TK) inhibitor.

Also provided are methods of treating, inhibiting, or delaying the onset of cancer in a subject. The method comprises the step of administering a therapeutically effective amount of a keratinocyte growth factor receptor tyrosine kinase (KGFR TK) inhibitor to the subject in need of such treatment. The KGFR TK inhibitors are expected to be effective in the treatment breast, uterine, ovarian, cervical, colon, rectal, stomach, thyroid, lung, testicular, kidney, bladder, trachea, small intestine, vulva, liver, pancreatic, prostate, and other cancers in humans and other subjects that may need treatment for cancer. In a preferred embodiment, the KGFR TK inhibitor is one of compound I, II, or III, or combinations thereof.

The KGFR TK inhibitors provided herein are especially effective in preventing the metastasis of cancers. They are expected to be useful in the treatment of metastatic cancers such as breast, uterine, ovarian, cervical, colon, rectal, stomach, thyroid, lung, testicular, kidney, bladder, trachea, small intestine, vulva, liver, pancreatic, prostate, and other metastatic cancers.

Figure 7A:
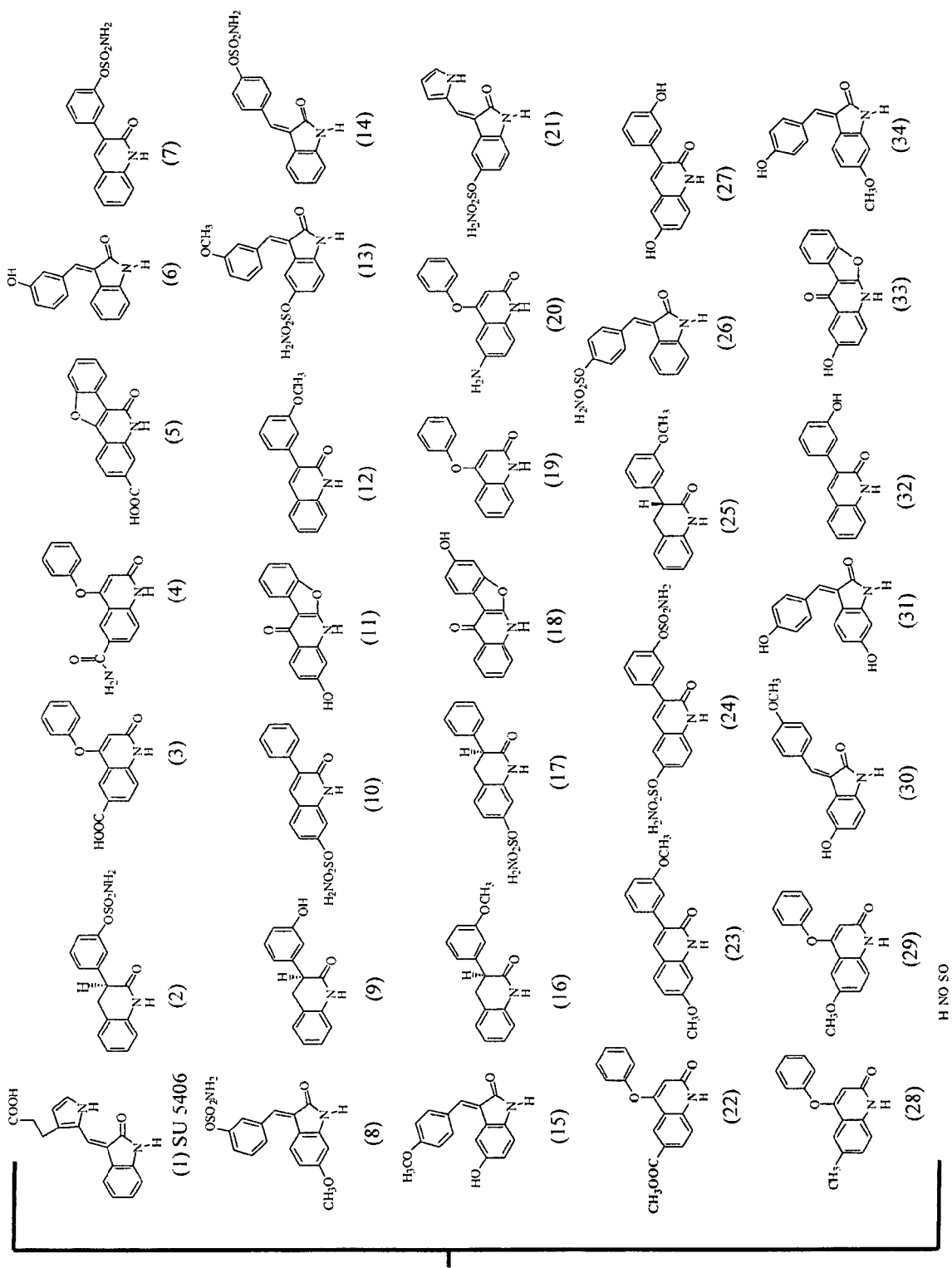
FIG. 7 show a virtual library of KGFR inhibitors containing structures of indolinones, quinolinones and their conformationally restricted analogs. The compounds are prioritized with the compound having the highest free binding energy ranked compound 1 (SU5402).
Figure 7B:
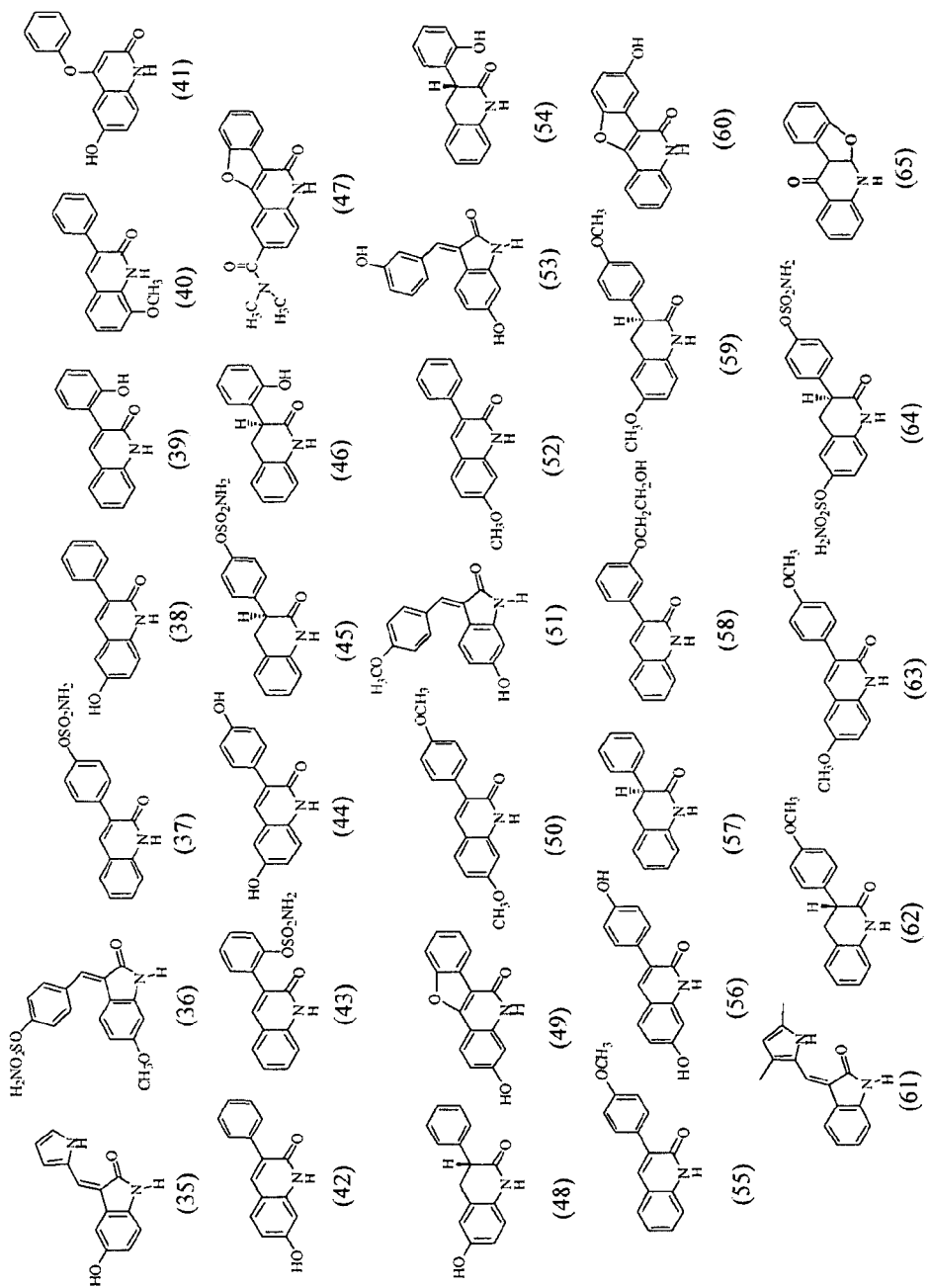

The keratinocyte growth factor receptor-tyrosine kinase (KGFR TK) specific inhibitors described herein are shown in FIG. 7. These further include derivatives, pharmaceutically acceptable salts, and metabolites thereof. The methods of using the KGFR TK inhibitors described herein in the treatment or prevention of metastasis in a subject comprise administering a therapeutically effective amount of a KGFR TK inhibitor described herein to a subject in need of such treatment. In one embodiment, the method is a method of treating cancer in a subject comprising the step of administering a therapeutically effective amount of a KGFR TK inhibitor described herein to a subject diagnosed with cancer. In one embodiment, the method comprises a method of treating cancer in a subject comprising the step of administering a therapeutically effective amount of a KGFR TK inhibitor described herein to a subject having cancer. Also provided are methods of preventing the proliferation of unwanted proliferating cells in a subject, the method comprising the step of administering a therapeutically effective amount of a KGFR TK inhibitor described herein to a subject at risk of developing a condition characterized by unwanted proliferation cells. In one embodiment, the method is a method of preventing cancer. In another embodiment, the method is a method of preventing cancer. In some embodiments, the methods treating unwanted proliferating cells, including cancers and precancers, comprise inducing apoptosis in the unwanted proliferating cells by administering an effective amount of the KGFR TK inhibitor to the subject in need of such treatment.

As used herein, the term "prevention" includes preventing the onset of a clinically evident unwanted cell proliferation altogether; and preventing the onset of a preclinically evident stage of unwanted rapid cell proliferation in a subject at risk for developing a condition characterized by unwanted cell proliferation, such as cancer; as well as preventing the onset of metastasis in a subject that has been diagnosed with cancer. Also intended to be encompassed by this definition is the prevention of metastasis of malignant cells or to arrest or reverse the progression of malignant cells. This includes prophylactic treatment of those at risk of developing precancers and cancers.

The terms "therapeutically effective" and "pharmacologically effective" are intended to qualify the amount of each agent which will achieve the goal of improvement in disease severity and the frequency of incidence, while avoiding adverse side effects typically associated with conventional cancer chemotherapy.

The term "subject" for purposes of treatment includes any human or animal subject who has a disorder characterized by unwanted, rapid cell proliferation. Such disorders include, but are not limited to cancers and precancers. For methods of prevention the subject is any human or animal subject, and preferably is a human subject who is at risk of obtaining a disorder characterized by unwanted, rapid cell proliferation, such as cancer. The subject may be at risk due to exposure to carcinogenic agents, being genetically predisposed to disorders characterized by unwanted, rapid cell proliferation, and so on. Besides being useful for human treatment, the compounds of the present invention are also useful for veterinary treatment of mammals, including companion animals and farm animals, such as, but not limited to dogs, cats, horses, cows, sheep, and pigs. In most embodiments, subject means a human.

The phrase "pharmaceutically acceptable salts" connotes salts commonly used to form alkali metal salts and to form addition salts of free acids or free bases. The nature of the salt is not critical, provided that it is pharmaceutically acceptable. Suitable pharmaceutically acceptable acid addition salts of the KGFR TK inhibitors described herein may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic, and sulfonic classes of organic acids, examples of which include formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, ambonic, pamoic, methanesulfonic, ethanesulfonic, benzenesulfonic, pantothenic, 2-hydroxyethanesulfonic, toluenesulfonic, sulfanilic, cyclohexylaminosulfonic, stearic, algenic, β-hydroxybutyric, galactaric, and galacturonic acids. Suitable pharmaceutically acceptable base addition salts of the compounds described herein include metallic salts made from aluminum, calcium, lithium, magnesium, potassium, sodium, and zinc. Alternatively, organic salts made from N,N'-dibenzylethylenediamine, chloroprocaine, choline, diethanolamine, ethylenediamine, meglumine (N-methylglucamine) and procaine may be used to form base addition salts of the compounds described herein. All of these salts may be prepared by conventional means from the corresponding compounds described herein by reacting, for example, the appropriate acid or base with the compound.

Where the term alkyl is used, either alone or with other terms, such as haloalkyl or alkylaryl, it includes $C_1$ to $C_{10}$ linear or branched alkyl radicals, examples include methyl, ethyl, propyl, isopropyl, butyl, tert-butyl, and so forth. The term "haloalkyl" includes $C_1$ to $C_{10}$ linear or branched alkyl radicals substituted with one or more halo radicals. Some examples of haloalkyl radicals include trifluoromethyl, 1,2-dichloroethyl, 3-bromopropyl, and so forth. The term "halo" includes radicals selected from F, Cl, Br, and I. Alkyl radical substituents of the present invention may also be substituted with other groups such as azido, for example, azidomethyl, 2-azidoethyl, 3-azidopropyl and so on.

The term aryl, used alone or in combination with other terms such as alkylaryl, haloaryl, or haloalkylaryl, includes such aromatic radicals as phenyl, biphenyl, and benzyl, as well as fused aryl radicals such as naphthyl, anthryl, phenanthrenyl, fluorenyl, and indenyl and so forth. The term "aryl" also encompasses "heteroaryls," which are aryls that have carbon and one or more heteroatoms, such as O, N, or S in the aromatic ring. Examples of heteroaryls include indolyl, pyrrolyl, and so on. "Alkylaryl" or "arylalkyl" refers to alkyl-substituted aryl groups such as butylphenyl, propylphenyl, ethylphenyl, methylphenyl, 3,5-dimethylphenyl, tert-butylphenyl and so forth. "Haloaryl" refers to aryl radicals in which one or more substitutable positions has been substituted with a halo radical, examples include fluorophenyl, 4 chlorophenyl, 2,5 chlorophenyl and so forth. "Haloalkylaryl" refers to aryl radicals that have a haloalkyl substituent.

Provided are pharmaceutical compositions for inhibiting KGFR TK mediated signal transduction pathways specifically. These compounds are also useful for treating, preventing, or delaying the onset of a cancer and treating and preventing metastasis in a subject in need of such treatment. The pharmaceutical composition comprises a therapeutically effective amount of a compound disclosed herein, or a derivative or pharmaceutically acceptable salt thereof, in association with at least one pharmaceutically acceptable carrier, adjuvant, or diluent (collectively referred to herein as "carrier materials") and, if desired, other active ingredients. The active compounds of the present invention may be administered by any suitable route known to those skilled in the art, preferably in the form of a pharmaceutical composition adapted to such a route, and in a dose effective for the treatment intended. The active compounds and composition may, for example, be administered orally, intra-vascularly, intraperitoneally, intranasal, intrabronchial, subcutaneously, intramuscularly or topically (including aerosol and sustained release patch). With some subjects local administration, rather than system administration, may be preferred. Formulation in a lipid vehicle may be used to enhance bioavailability.

The administration of the present invention may be for either prevention or treatment purposes. The methods and compositions used herein may be used alone or in conjunction with additional therapies known to those skilled in the art in the prevention or treatment of disorders characterized by unwanted, rapid proliferation of cells. Alternatively, the methods and compositions described herein may be used as adjunct therapy. By way of example, the compounds of the present invention may be administered alone or in conjunction with other antineoplastic agents or other growth inhibiting agents or other drugs or nutrients, as in an adjunct therapy.

The phrase "adjunct therapy" or "combination therapy" in defining use of a compound described herein and one or more other pharmaceutical agents, is intended to embrace administration of each agent in a sequential manner in a regimen that will provide beneficial effects of the drug combination, and is intended as well to embrace co-administration of these agents in a substantially simultaneous manner, such as in a single formulation having a fixed ratio of these active agents, or in multiple, separate formulations for each agent.

For the purposes of combination therapy, there are large numbers of antineoplastic agents available in commercial use, in clinical evaluation and in pre-clinical development, which could be selected for treatment of cancers or other disorders characterized by rapid proliferation of cells by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents. Alternatively, other anti-neoplastic agents, such as metallomatrix proteases inhibitors (MMP), such as MMP inhibitors, or $α_ν β_3$ inhibitors may be used. Suitable agents which may be used in combination therapy will be recognized by those of skill in the art. Similarly, when combination therapy is desired, radiation may also be used.

When preparing the compounds described herein for oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable carrier.

For intravenous, intramuscular, subcutaneous, or intraperitoneal administration, the compound may be combined with a sterile aqueous solution which is preferably isotonic with the blood of the recipient. Such formulations may be prepared by dissolving solid active ingredient in water containing physiologically compatible substances such as sodium chloride, glycine, and the like, and having a buffered pH compatible with physiological conditions to produce an aqueous solution, and rendering said solution sterile. The formulations may be present in unit or multi-dose containers such as sealed ampoules or vials.

For treating cancers or other unwanted proliferative cells that are localized in the G.I. tract, the compound may be formulated with acid-stable, base-labile coatings known in the art which begin to dissolve in the high pH small intestine. Formulation to enhance local pharmacologic effects and reduce systemic uptake are preferred.

Formulations suitable for parenteral administration conveniently comprise a sterile aqueous preparation of the active compound which is preferably made isotonic. Preparations for injections may also be formulated by suspending or emulsifying the compounds in non-aqueous solvent, such as vegetable oil, synthetic aliphatic acid glycerides, esters of higher aliphatic acids or propylene glycol.

The dosage form and amount can be readily established by reference to known treatment or prophylactic regiments. The amount of therapeutically active compound that is administered and the dosage regimen for treating a disease condition with the compounds and/or compositions of this invention depends on a variety of factors, including the age, weight, sex, and medical condition of the subject, the severity of the disease, the route and frequency of administration, and the particular compound employed, the location of the unwanted proliferating cells, as well as the pharmacokinetic properties of the individual treated, and thus may vary widely. The dosage will generally be lower if the compounds are administered locally rather than systemically, and for prevention rather than for treatment. Such treatments may be administered as often as necessary and for the period of time judged necessary by the treating physician. One of skill in the art will appreciate that the dosage regime or therapeutically effective amount of the inhibitor to be administered may need to be optimized for each individual. The pharmaceutical compositions may contain active ingredient in the range of about 0.1 to 2000 mg, preferably in the range of about 0.5 to 500 mg and most preferably between about 1 and 200 mg. A daily dose of about 0.01 to 100 mg/kg body weight, preferably between about 0.1 and about 50 mg/kg body weight, may be appropriate. The daily dose can be administered in one to four doses per day or by continuous infusion from a parenteral or topical source.

Preliminary Studies

Based on this background information, we examined the motility effect of KGF on human breast cancer cells using time-lapse videomicroscopy and culture wounding (22, 23). We observed that recombinant human KGF produces a cell scattering motility effect on MCF-7 human cancer cells. The KGF motility effect is characterized by a rapid increase in ruffling of the plasma membrane and cell scattering. The maximal KGF motility effect occurred within one hour and the change in morphology of the MCF-7 cells was observed to last for a period of at least 48 hours. In these experiments with KGF-treated MCF-7 cells, we observed a dose-related increase in the perimeter index (PI; which measures membrane protrusions; indicative of motile cell morphology) and a similar increase in fast plasma membrane movements (FPMM; which measures movement of peripheral cell membranes; also indicative of cellular motility). Scanning electron microscopy of KGF-treated MCF-7 cells confirmed dramatic changes in cell morphology consistent with active cell motility (FIG. 1). Pretreatment with a monoclonal antibody to KGF neutralized the motility response; thus demonstrating the specificity of this response to KGF (22). Changes in cell morphology, associated with membrane ruffling and motility are believed to be associated with cytoskeletal reorganization and necessary for adhesion foci, cell surface ligand-receptor binding and regulation of gene transduction (24, 25). Accordingly, we have previously observed a significant alteration in the distribution of f-actin in the cytoplasm of KGF stimulated MCF-7 cells (22).

In our previous experiments, all of the estrogen receptor (ER)-positive human breast cancer cell lines examined (MCF-7, T-47D, ZR-75-1) responded to KGF treatment (10-50 ng/ml); however, the responsiveness differed substantially among the cell lines tested. The order of responsiveness of the ER-positive cell lines was found to be MCF-7>T-47D>ZR-75-1. Conversely, KGF treatment produced little or no enhancement in the motility of ER-negative cells lines examined (MDA-MB-231, SK-BR-3, BT-20) in this study (23).

These results support our concept that the KGF-KGFR induced stimulation of cell motility is an early event in the metastatic progression of breast cancer. This concept is further supported by a recent experiment in which we used a cancer array (BD Clontech) spotted with cDNA from 10 random human breast cancer samples (26). The results of probing the array with a 461 base pair KGFR cDNA probe demonstrated that 6 of the 10 breast cancer samples on the array expressed higher levels of KGFR than normal tissue from the same patient. The KGFR cDNA probe did not hybridize to the negative controls on the array which include total yeast RNA, $E.$ $Coli$ DNA, Poly A and a human DNA tandem repeat; however, the probe did hybridized to the human genomic DNA positive control. All six of the breast tumor specimens with a higher level of KGFR expression were observed to be in situ tumors, at an early stage of cancer development (stage I). In addition, we observed that KGFR was over-expressed in uterine, ovarian, cervical, colon, rectal, stomach, thyroid, lung, testicular, kidney, bladder, trachea, small intestine, vulva, liver, pancreatic and prostate cancer samples when compared to normal tissue from the same patient. These data suggest that KGFR may be an important therapeutic target in many types of cancer.

In order to determine the influence of KGF on tumor growth and development in vivo, we recently examined the effect of KGF treatment on the growth and metastasis of MCF-7 cells in a nude mouse xenograft model (27, 28). In these experiments $5 \times 10^6$ viable MCF-7 cells, transfected with a β-gal reporter plasmid, were embedded into 0.2 ml Matrigel and implanted into female nu/nu balb/C mice at 6 weeks of age. At 40 days after tumor cell implantation, when approximately 0.5 cm tumor masses were observed, animal were treated with either human recombinant KGF or control vehicle by intra-tumoral injections every other day for a period of 21 days. It was observed that the tumor volume in the KGF treated tumors was the same as in the control tumors. In tumor and tissue samples, collected at the end of the treatment period, the β-gal activity was used as a reported to quantify MCF-7 cells as previously described (27). In this study, the β-gal activity in the KGF treated tumor tissue was significantly less than in the controls. However, in the connective tissue surrounding the tumors and in the lung and liver tissue samples, the β-gal activity was much greater in the KGF treated than in the control samples (FIG. 2) (28). The results of the present study indicate that KGF enhances the migration of breast cancer cells away from the tumor mass, resulting in measurable lung and liver metastasis within the 21 day treatment period. These results further support the concept that KGF from stromal tissue and/or KGFR up-regulation in cancer cells may be an early signal in the metastatic progression of breast cancer.

In order to define the signaling pathway involved in the KGF-mediated breast cancer cell motility, we have examined the influence of inhibitors of intermediates in the TK signaling pathway (29, 30, 31). We observed that genistein (tyrosine kinase inhibitor) and PD98059 (MEK inhibitor) completely abolished KGF-mediated motility of MCF-7 cells. In addition, inhibition of Grb2, using a specific Grb2 antisense oligonucleotide, abolished KGF-mediated motility of MCF-7 cells (30, 31). A representative Western blot demonstrating a KGF-induced increase in the phospho-Erk1,2 protein and inhibitor-induced inhibition of baseline and KGF stimulated Erk1,2 levels is shown in FIG. 3. Thus, we have observed that the KGFR-Erk1,2 pathway mediates KGF-induced cell motility in ER-positive breast cancer cells. Accordingly, inhibitors targeting the KGF/KGFR/Grb2/Erk1,2 pathway have the potential to be selective therapeutic or chemopreventive modalities against breast cancer metastasis. Although the inhibitors tested in these experiments were not specific for KGFR inhibition, these results demonstrate that the development of highly selective KGFR TK inhibitors should abolish KGF-induced motility signaling associated with breast cancer metastatic progression. Thus we next considered the design of selective KGFR TK inhibitors to be examined in this study.

Development of Small-Molecule ATP-Competitive Inhibitors as Selective KGFR TK Inhibitors.

Since KGFR is a trans-membrane growth factor tyrosine kinase, the design of small molecule selective inhibitors of KGFR that compete with ATP for the catalytic site represents a viable approach. As all members of the kinase family bind the same nucleotide co-factor, the dogma in the field had been that the ATP-binding cleft of this enzyme class would not prove to be a good target for drug discovery. However, within the last several years a number of protein kinase selective ATP-competitive inhibitors, some of which show a high degree of selectivity, have been identified (32-35). The first ATP-competitive protein tyrosine kinase inhibitor Gleevec (ST1571) was approved in 2001 for the treatment of chronic myelogenous leukemia (CML) (36).

No known ATP-competitive KGFR antagonists have ever been reported. In addition, unlike other protein kinases, the X-ray crystal structure of the receptor is not known. Fortunately the x-ray crystal structure of FGFR1, another member of the FGFR family, is available. The FGFR-1 tyrosine kinase domain has been crystallized and structures determined in complex with inhibitors PD173074 (protein data bank (PDB) file# 2FGI), SU4984 (PDB # 1AGW), and SU5402 (PDB # 1FGI) and this protein has 86% homology with the KGFR tyrosine kinase domain (37-39). The amino acid sequence alignment of human KGFR (hKGFR), mouse KGFR (mKGFR) and FGFR-1 tyrosine kinase domains is shown below in FIG. 4.

We have constructed a homology model of the KGFR tyrosine kinase domain using 2FGI as a template, which was used to guide the design of novel ATP site-directed ligands. In silico site-directed mutagenesis was used to generate a model of the KGFR receptor tyrosine kinase domain.

Model Building and Refinement: All of the following techniques were conducted in Sybyl versions 6.7 or higher (Tripos Associates, St. Louis, Mo.). The crystal structure of the FGFR-1 tyrosine kinase domain bound to the inhibitor PD173074 (PDB # 2FGI) serves as the basis for the model. Amino acids Gly580 through Pro591 were missing from the structure. Loop searching in the Biopolymer module was used with N and C terminal anchor residues set to three. A single loop from 1BVP was identified and the conformation was copied to the corresponding FGFR-1 sequence. Mutation of the side chains of the FGFR-1 to the corresponding side chains of KGFR was performed with the "mutate monomer" command. Tyr654 was phosphorylated using the "modify monomer" command. After the mutations were completed, side chains are minimized using the AMBER 4.1 force field. The resulting KGFR tyrosine kinase domain was then immersed into a box of TIP3P water. An unrestrained molecular dynamics (MD) simulation was performed at 300 K for 50,000 fs, with a Boltzmann distribution of initial velocities. An 8 Å non-bonded interaction cutoff was used, and the non-bonded pairlist was updated every 25 fs. Structures were averaged over time periods in which the atoms had obtained a stable trajectory. The averaged structures were minimized to a gradient of 0.5 kcal/mol/angstrom, followed by 100 steps of deepest descent minimization. The crystal structure of FGFR-1 and KGFR homology model is shown below (FIG. 5). This model has identified some key residues in the KGFR tyrosine kinase domain, which differ from those found in FGFR-1. Alanine 488 of the FGFR-1 tyrosine domain corresponds to a Cys residue within KGFR, because of the polarity differences in these amino acids, ligands identified from virtual screening could be optimized to exploit a novel interaction. Another key difference in the tyrosine kinase domains of these proteins lies in a 12 amino acid stretch near the entrance to the ATP binding site (Asn589→Phe600-DINRVPE-EQMTF (SEQ ID NO: 1)). Two residues in this segment, Asn 586 and Pro 587 of FGFR-1, correspond to an aspartic acid and an isoleucine; respectively, in KGFR (FIG. 5). The lack of conformationally restricted proline in KGFR in that segment may result in a different secondary structure near the ATP binding site. The opportunity for interaction with other amino acids by selective ligands may emerge as the result of molecular dynamic simulations.

Figure 6:
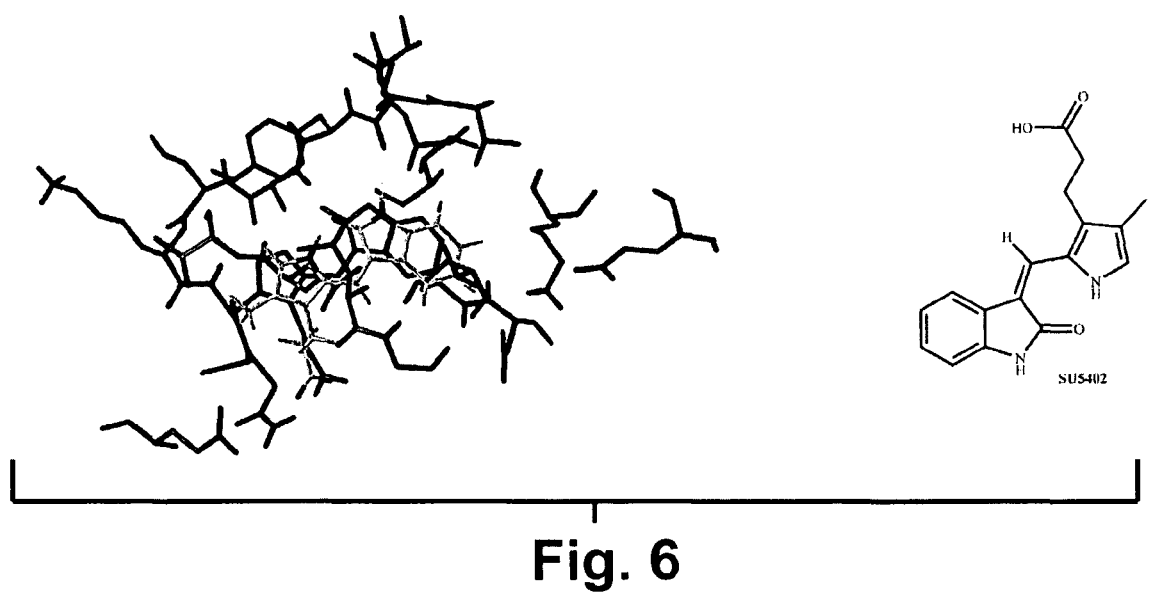
FIG. 6 FlexX reproduces the binding mode of SU5402 in 1FGI with an RMS deviation of 1.08 angstroms. Protein, reference ligand, and docked SU5402 (by atom type) are shown. Hydrogen bonds are shown as dotted lines.

Virtual screening of in-house libraries: Virtual screening of the combinatorial libraries is performed with FlexX within the Sybyl environment. This is a flexible docking method that uses an incremental construction algorithm to place ligands into the active site. When performing docking of ligands in FGFR-1, the bound ligands were used as a reference and the binding pocket was defined by amino acids in a 6.5 Å sphere from ligand atoms. To validate the docking method, we tested its ability to reproduce the binding mode of SU5402 in 1FGI (FIG. 6). To prepare the KGFR homology model for docking, all of the hydrogens were removed. In all cases ligands were docked with hydrogens present and formal charges were assigned to all atoms. Because the KGFR homology model lacked a bound ligand, the corresponding amino acids to those identified in FGFR-1 plus a 2.5 Å selection radius was used to create the receptor description file. The ranking of the generated solutions is performed using a scoring function that estimates the free binding energy of the protein-ligand complex.

Figure 8:
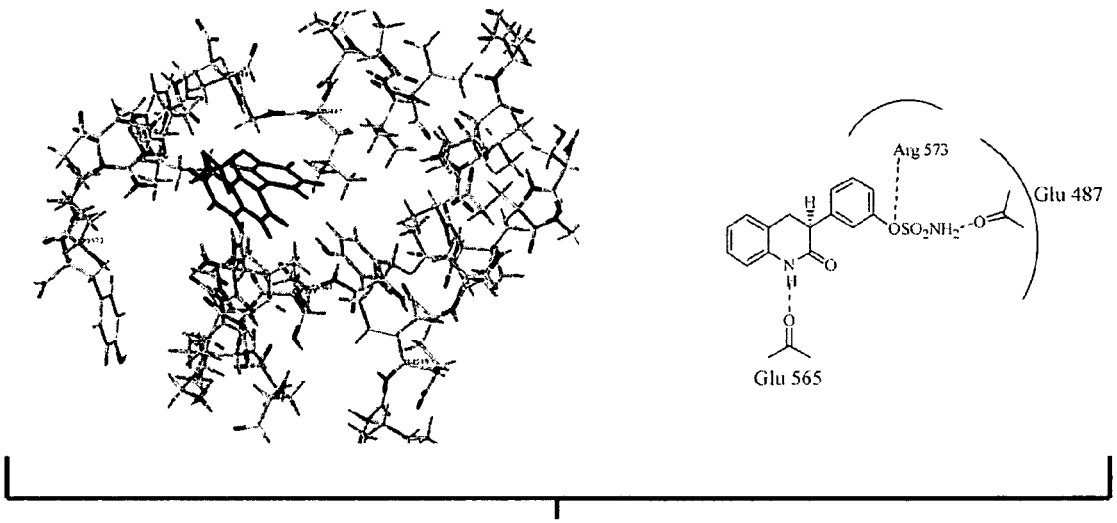
FIG. 8 shows the binding of compound 2 to the homology model of the ATP pocket of KGFR.

We have been involved in the design and synthesis protein tyrosine kinase ATP-competitive inhibitors for several years. Specifically we have designed inhibitors that target vascular endothelial growth factor (VEGF) and cyclin dependent kinase (CDK). Currently we have a series of potential inhibitors of KGFR in our in-house virtual library. The library contains compounds with indolinone and quinolinone structural cores and their conformationally restricted analogs (FIG. 7). They are indolinone (compounds 1, 6, 8, 13-15, 21, 26, 30-31, 34-36, 51, 53 and 61), dihydroquinolinones (compounds 2, 9, 16-17, 25, 45-46, 48, 57, 59, 62 and 64), quinolinones (compounds 3-4, 7, 10, 12, 19-20, 22-24, 27-29, 32, 37-44, 50, 52, 55-56, 58 and 63), benzofuro (3,2-c) quinolinones (compounds 5, 47, 49 and 60) and benzofuro (2,3-b) quinolinones (compounds 11, 18, 33 and 65). Virtual screening of the library was performed with FlexX within the Sybyl environment. The ranking of the generated solutions was performed using a scoring function that estimates the free binding energy of the protein-ligand complex. The molecule with the highest estimated free binding energy is ranked 1. As expected, compound 1 (SU5402) is ranked the highest in terms of estimated binding energy. The top five compounds with the highest estimated free binding energy contain the indolinone (compound 1), dihydroquinolinone (compound 2), quinolinones (compounds 3 and 4) and benzofuro (3,2-c) quinolinones (compound 5) structural cores. The binding of compound 2 to the homology model of the ATP pocket of KGFR is similar to SU 5402 (FIG. 8).

Figure 9:
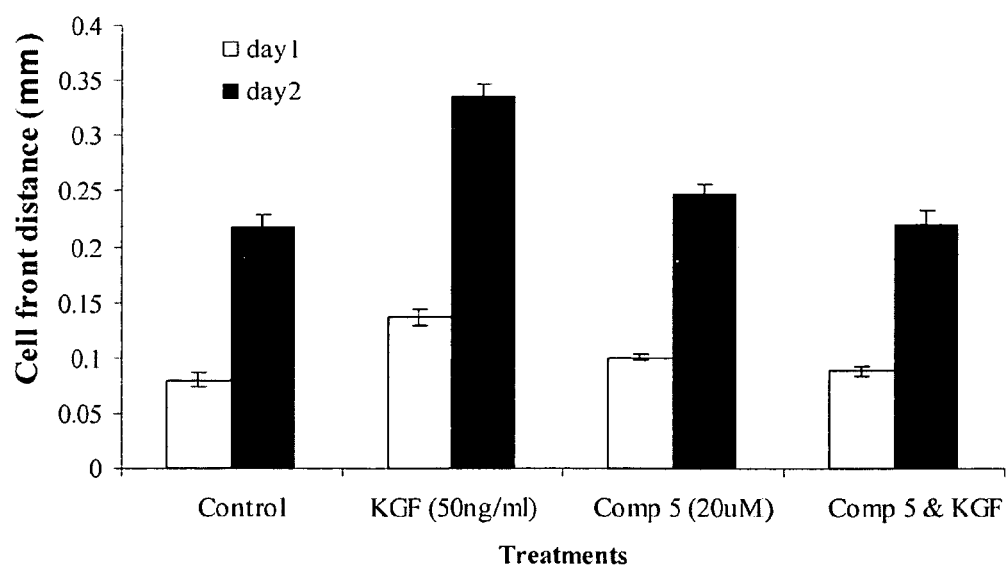
FIG. 9 shows the influence of compound 5 on KGF-mediated cell motility. MCF-7 cells were treated with either KGF (50 ng/ml), compound 5 (20 µM) or the combination at the time of culture wounding and cell migration was measured at 24 and 48 hours. Each bar represents of the mean of 10-15 observations±SEM.

We have examined the influence of one of the prototype KGFR TK inhibitor compounds (compound 5 in FIG. 7) on KGF-mediated migration of MCF-7 cells in a culture wounding model. We observed that treatment of MCF-7 cell cultures with compound 5 (20 μM) completely abolished KGF-induced cell migration (FIG. 9). Interestingly, we also observed that compound 5 produced a marked reduction in KGFR density of the MCF-7 cells by immunocytochemistry (FIG. 10). Receptor modeling described above indicates that compound 5 binds selectively and with high affinity to the KGFR. Thus, our preliminary studies with this prototype KGFR TK inhibitor indicates that our receptor modeling is capable of predicting highly effective and selective KGFR TK inhibitors which have the potential to be useful therapeutically in the prevention of cancer metastatic progression.

Because KGF is capable of profound stimulation of breast cancer cell proliferation and motility, specific inhibition of KGF-mediated receptor signaling at the KGFR TK receptor should reduce or eliminate the KGF-associated effects on cancer motility and metastatic activity which we have previously observed both in vitro and in vivo.

Experimental

Design and synthesis of the KGFR TK inhibitors: In our preliminary studies we have shown that compound 5 at 20 μM completely inhibited KGF-induced cell migration. Our molecular modeling predicted compound 5 to have a high affinity to the KGFR model at the ATP binding site. Since compound 5 (containing a benzofuro (3,2-c) quinolinone moiety) is conformationally highly constrained, several classes of analogs are designed to have different degrees of flexibility (FIG. 11). They are, 4-phenoxy-quinolinone, 3-phenyl-quinolinone, indolinone and benzofuro (2,3-b)-quinolinone. We have synthesized several analogs in each class and the syntheses of the compounds are described below.

Figure 12:
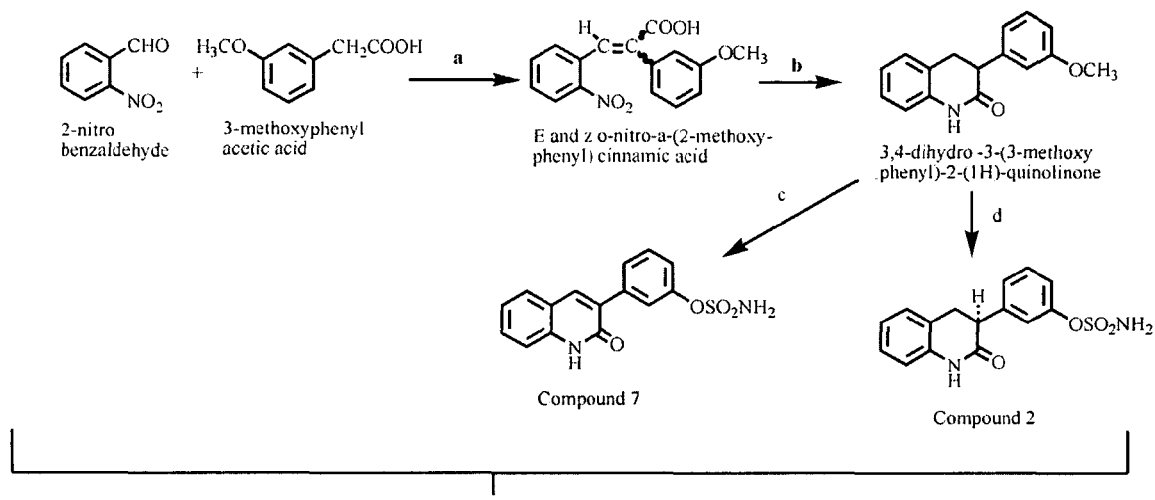
FIG. 12 shows the synthesis of compound 2 and 7. Reagents: a.—Ac2O, TEA, reflux 2.5 hr; b.—5% Pd—C/H$_2$, CH$_3$OH, r.t, 18 hr; c. (i.)—DDQ, ClCH$_2$CH$_2$Cl, reflux 48 hr; c. (ii.)—BBr3, CH$_2$Cl$_2$, r.t 2.5 hr; c. (iii.)—ClSO$_2$NH$_2$, NaH, DMF, r.t, 24 h.

Synthesis of 3-phenyl-quinolinone (compounds 2 and 7): The synthesis of compounds 2 and 7 are shown in FIG. 12. The quinolinone core in compounds 2 and 7 was synthesized with a published procedure (40). In brief, refluxing 2-nitrobenzaldehyde with 3-methoxyphenyl acetic acid in the presence of acetic anhydride yielded E and Z o-nitro-a-(2-methoxy-phenyl) cinnamic acid. Reduction of the nitro group in the cinnamic acid with concomitant cyclization yielded 3,4-dihydro-3-(3-methoxyphenyl)-2-(1H)-quinolinone. Compound 2 was obtained by demethylation following by sulfamoylation (41).

Figure 13:
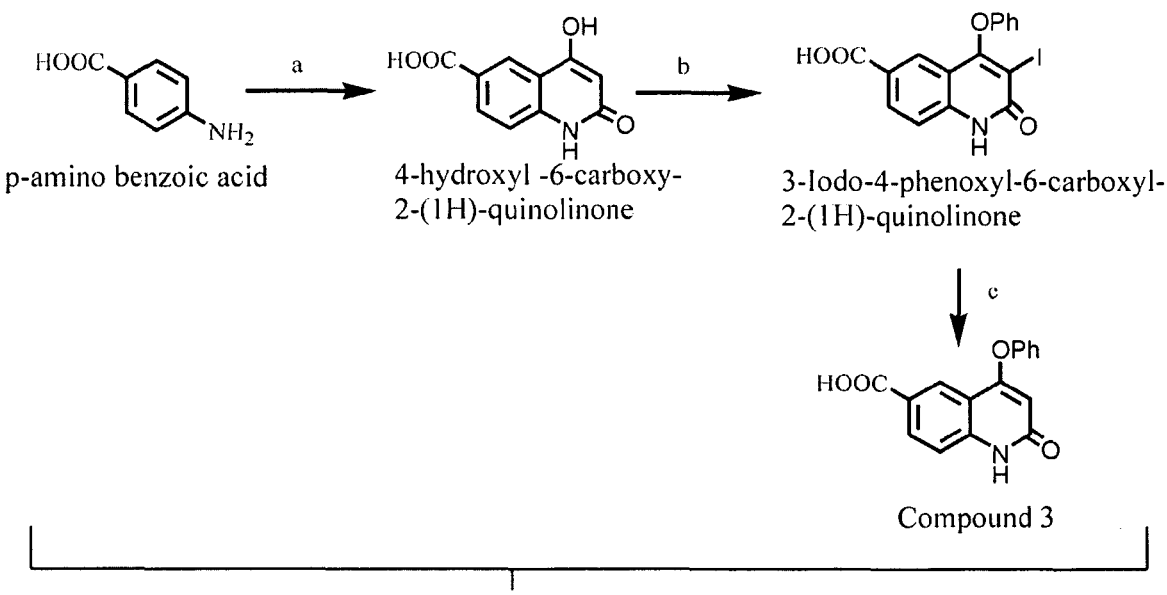
FIG. 13 shows the synthesis of compound 3; Reagents: a.—CH$_2$(COOH)$_2$, POCl$_3$/ZnCl$_2$; b. (i).—Ph-ICl$_2$, NaHCO$_3$; b. (ii).—n-BuOH/Reflux; c.—Zn/AcOH, EtOH.

Synthesis of 4-phenoxyquinoline (compound 3): The 4-phenoxyquinoline core structure was synthesized according to a published procedure (42). The synthesis of compound 3 is described in FIG. 13. The synthesis began with stirring p-aminobenzoic acid with malonic acid and phosphorus oxychloride to yield 4-hydroxy-6-carboxy-2-(1H)-quinolinone. Reacting the quinolinone with dichloroiodobenzene is followed by refluxing with butanol produced 3-Iodo-4-phenoxyl-6-carboxyl-2-(1H)-quinolinone. Diodination of the 3-iodo quinolinone yielded compound 3.

Figure 14:
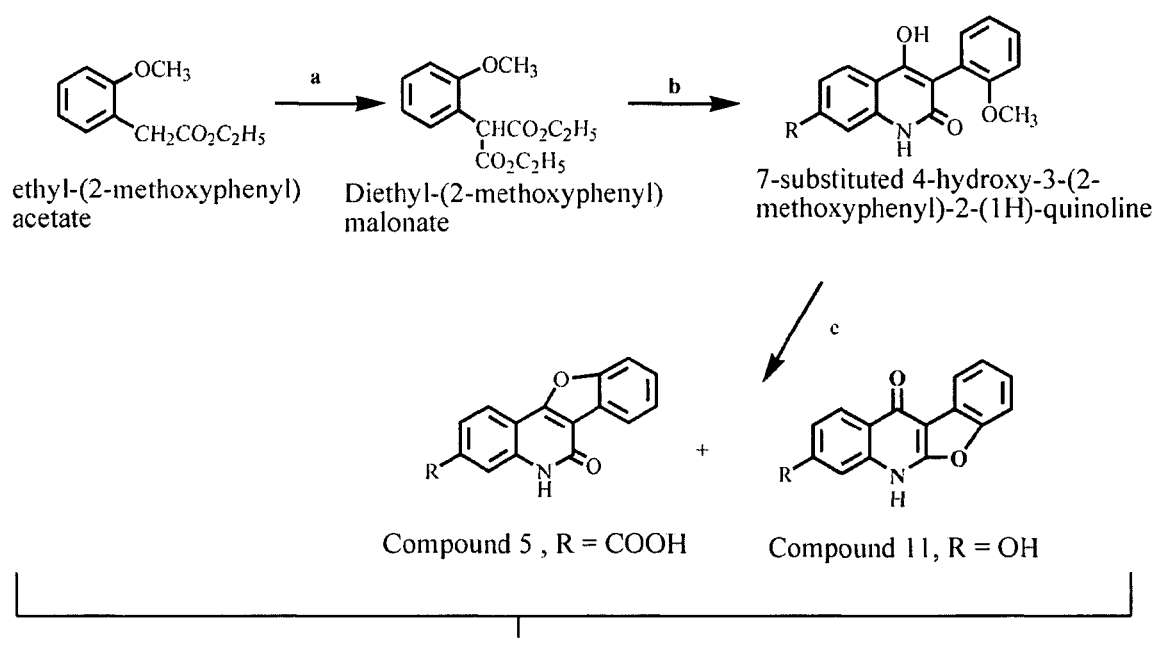
FIG. 14 shows the synthesis of compounds 5 and 11; Reagents: a. (i.)—Diethyl oxalate, EtOK, benzene, 60° C., 30 min; a. (ii.)—175° C., —CO; b.—m-substituted aniline (substituted group are either COOH or OH), Ph2O, reflux 3.5 hr; c.—anhydrous pyridine hydrochloride, reflux 1.5 hr.

Synthesis of benzofuro (3,2-c) and benzofuro (2,3-b) quinolinones (compounds 5 and 11): The synthesis of compounds 5 and 11 are shown in FIG. 14 with a similar procedure reported previously (43, 44). In brief, the synthesis first involved the formation of diethyl-(2-methoxy phenyl) malonate by heating ethyl-(2-methoxyphenyl)acetate with diethyl oxalate followed by thermal decarbonylation. Refluxing diethyl-(2-methoxy phenyl) malonate with m-substituted aniline in diphenylether yielded 7-substituted 4-hydroxy-3-(2-methoxyphenyl)-2-(1H)-quinoline. Compounds 5 and 7 were obtained by refluxing the substituted quinoline in anhydrous pyridine hydrochloride.

The synthesis of inhibitors with indolinone moieties will be accomplished as previously described (45, 46).

The examples herein are for illustrative purposes only and are not meant to limit the scope of the invention.

LITERATURE CITED

1. Rubin J S, Bottaro D P, Chedid M, Miki T, Ron D, Cunha G R, P W Finch. Keratinocyte growth factor as a cytokine that mediates mesenchymal-epithelial interaction. in "Epithelial-Mesenchymal Interactions in Cancer" (I D Goldberg & E M Rosen, eds) Verlag Basel. 74:191-214 (1995).
2. Rubin J S, Osada H, Finch P W, Taylor W G, Rudikoff S, Aaronson S A. Purification and characterization of a newly identified growth factor specific for epithelial cells. Proc Natl Acad Sci USA. 86:802-806 (1989).
3. Baird A, Klagsbrun M. The fibroblast growth factor family; Nomenclature meeting report and recommendations. Ann NY Acad Sci. 638: 13-16 (1991).
4. Bottaro D P, Rubin J S, Ron D, Finch P W, Florio C, Aaronson S A. Characterization of the receptor for keratinocyte growth factor. Evidence for multiple fibroblast growth factor receptors. J Biol Chem. 265:12767-12770 (1990).
5. Aaronson S A, Bottaro D P, Miki T, Ron D, Finch P W, Fleming T P, Ahn J, Taylor W G, Rubin J S. Keratinocyte growth factor. A fibroblast growth factor family member with unusual target cell specificity. Ann NY Acad Sci. 638:62-77 (1991).
6. Miki T, Fleming T P, Bottaro D P, Rubin J S, Ron D, Aaronson S A. Expression cDNA cloning of the KGF receptor by creation of a transforming autocrine loop. Science. 251:72-75 (1991).
7. Mason I J, Fuller-Pace F, Smith R, Dickson C. FGF-7 (keratinocyte growth factor) expression during mouse development suggests roles in myogenesis, forebrain regionalization and epithelial-mesenchymal interactions. Mech Dev. 45:15-30 (1994).
8. Ulich T R, Yi E S, Cardiff R, Yin S, Bikhazi N, Biltz R, Morris C F, Pierce G F. Keratinocyte growth factor is a growth factor for mammary epithelium in vivo. The mammary epithelium of lactating rats is resistant to the proliferative action of keratinocyte growth factor. Am J Pathol. 144:862-868 (1994).
9. Kitsberg D I, Leder P. Keratinocyte growth factor induces mammary and prostatic hyperplasia and mammary adenocarcinoma in transgenic mice. Oncogene. 13(12):2507-2515 (1996).
10. Koos R D, Banks P K, Inkster S E, Yue W, Brodie A M. Detection of aromatase and keratinocyte growth factor expression in breast tumors using reverse transcription-polymerase chain reaction. J Steroid Biochem Mol Biol. 45:217-225 (1993).
11. Bansal G S, Cox H C, Marsh S, Gomm J J, Yiangou C, Luqmani Y, Coombes R C, Johnston C L. Expression of keratinocyte growth factor and its receptor in human breast cancer. J Brit Cancer. 75(11):1567-1574 (1997).

12. Zang X-P Learner M L, Brackett D J, Pento J T. KGF-induced gene expression in MCF-7 cells using cDNA expression arrays. Breast Cancer Res Treat. 2000; 64: 110.
13. Aznavoorian S, Murphy A N, Stetler-Stevenson W G, Liotta L A. Molecular aspects of tumor cell invasion and metastasis. Cancer 1993; 71: 1368-1383.
14. Ornitz D M, Xu J, Colvin J S, McEwen D G, MacAuthur C A, Coulier F, Gao G, Goldfarb M. Receptor specificity of the fibroblast growth factor family. J Biol Chem. 1996; 271: 15292-297.
15. Miki T, Fleming T P, Bottaro D P, Rubin J S, Ron D, Aaronson S A. Expression cDNA cloning of the KGF receptor by creation of a transforming autocrine loop. Science 1991; 251: 72-75.
16. Yan G, Fukabori Y, McBride G, Nikolaropolous S, McKeehan W L. Exon switching and activation of stromal and embryonic FGF receptor genes in prostate epithelial cell accompany stromal independence and malignancy. Molec Cell Biol 1993; 13: 4513-4522.
17. Powers C J, McLeskey S W, Wellstein A. Fibroblast growth factors, their receptors and signaling. Endo-Related Cancer. 2000; 7: 165-197.
18. Klijn J G M, Berns P M J J, Schmitz P I M, Foekens J A. The clinical significance of epidermal growth factor receptor (EGFR) in human breast cancer: A review on 5232 patients. Endocrine Rev. 1992; 13: 3-17.
19. Siansbury J R C, Farndon J R, Needham G K, Malcolm A J, Harris A L. Epidermal growth factor receptor status as predictor of early recurrence of and death from breast cancer. Lancet 1987; 1: 1398-1402.
20. Woodburn J R. The epidermal growth factor receptor and its inhibition in cancer therapy. Pharmacol Ther 1999; 82: 241-250.
21. Janmaat M L, Giaccone G. The EGF receptor pathway and its inhibition as anticancer therapy. Drugs Today 2003; 39: 61-80.
22. Rajah T T, Rambo D J, Dmytryk J J, Pento J T. Influence of antiestrogens on NIH-3T3-fibroblast-induced motility of breast cancer cells. Chemotherapy 2001; 47: 56-69.
23. Zang X-P, Pento J T. Keratinocyte growth factor-induced motility of breast cancer cells. Clin Eptl Metastasis 2001; 18: 573-580.
24. Cheng T P O. Minipodia, novel structures for extension of the lamella: A high-spatial-resolution video microscopic study. Exp Cell Res 1992; 203:25-31.
25. Van Larebeke N A F, Bracke M E, Mareel M M. Invasive epithelial cells show more fast plasma membrane movements than related or parental non-invasive cells. Cytometry 1992; 13: 9-14.
26. Zang X-P, Lerner M L, Brackett D J, Pento J T. A comparison of keratinocyte growth factor receptor expression in breast and other cancer tissue. Breast Cancer Res. Treat. 2003; 82: 525.
27. Buller C J, Zang X-P, Howard E W, Pento J T. Measurement of beta-galactosidase tissue levels in a tumor cell xenograft model. Meth Findings Exptl Pharmacol, 2003; 25: 713-716.
28. Buller C J, Zang X-P, Lerner M R, Brackett D J, Pento J T. Influence of KGF on breast cancer metastasis in nude mouse xenografts, Breast Cancer Res Treat 2003; 82: 380.
29. Nguyen T X, Nguyen T N, Zang X P, Pento J T. KGF signal transduction pathways involved in breast cancer cell metastasis, OUHSC GREAT Symp 2003; 25.
30. Zang X-P, Siwak D, Tari A M, Pento J T. Downregulation of Grb2 expression led to inhibition of KGF-induced motility in MCF-7 breast cancer cells. Breast Cancer Res Treat 2002; 76: 167.
31. Zang X-P, Siwak D, Nguyen T X, Tari A M, Pento J T. KGF-induced motility of breast cancer cells is dependent on Grb2 and Erk1,2. Clin Exptl Metastasis, Submitted.
32. Zwick E, Bange J, Ullrich A. Receptor tyrosine kinases as targets for anticancer drugs, Trends Mol Med. 2002; 8: 17-23.
33. Garcia-Echeverria C, Traxler P, Evans D B. ATP site-directed competitive and irreversible inhibitors of protein kinases, Med Res Rev. 2000; 20: 28-57.
34. Traxler P, Bold G, Buchdunger E, Caravatti G, Furet P, Manley P, O'Reilly T, Wood J, Zimmermann J. Tyrosine kinase inhibitors: from rational design to clinical trials, Med Res Rev. 2001; 21: 499-512.
35. Toledo L M, Lydon N B, Elbaum D. The structure-based design of ATP-site directed protein kinase inhibitors, Curr Med. Chem. 1999; 6: 775-805.
36. Druker B J. STI571 (Gleevec) as a paradigm for cancer therapy, Trends Mol Med. 2002; 8: 14-18.
37. Mohammadi M, Froum S, Hamby J M, Schroeder M C, Panek R L, Lu G H, Eliseenkova A V, Green D, Schlessinger J, Hubbard S R. Crystal structure of an angiogenesis inhibitor bound to the FGF receptor tyrosine kinase domain, Embo J. 1998; 17: 5896-904.
38. Mohammadi M, McMahon G, Sun L, Tang, C, Hirth P, Yeh B K, Hubbard S R, Schlessinger J. Structures of the tyrosine kinase domain of fibroblast growth factor receptor in complex with inhibitors, Science. 1997; 276: 955-960.
39. Mohammadi M, Schlessinger, J, Hubbard S R. Structure of the FGF receptor tyrosine kinase domain reveals a novel autoinhibitory mechanism, Cell. 1996; 86: 577-587.
40. Xiao Z, Waters N C, Woodard C L, Li Z, Li P K. Design and synthesis of Pfmrk inhibitors as potential antimalarial agents. Bioorg Med Chem Lett. 2001; 11: 2875-2878.
41. Li P K, Milano S, Kluth L, Rhodes M E. Synthesis and sulfatase inhibitory activities of nonsteroidal sulfatase inhibitor. J Steroid Biochem. Molec. Biol. 1996; 59: 41-48.
42. Kappe T, Korbuly G. Stadlbauer W. Ylides of heterocycles, II. Iodonium- and pyridinium ylides of malonyl heterocycles. Chemische Berichte. 1978; 111: 3857-66.
43. Yamaguchi S, Uchiucoh Y, and Sanada K. The synthesis of benzofuroquinolines. IX.A benzofuroisoquinoline and benzofuroisocoumarin. J. Heterocyclic Chem. 1995; 32: 419-423.
44. Yamada M, and Kawase Y. The synthesis of benzofuroquinolines. III. Two dihydroxybenzofuroquinolinones. J. Heterocyclic Chem. 1984; 21: 737-739.
45. Sun L, Tran N, Tang F, App H, Hirth P. Synthesis and biological evaluations of 3-substituted indolin-2-ones: a novel class of tyrosine kinase inhibitors that exhibit selectivity toward particular receptor tyrosine kinases. J Med Chem. 1998; 41: 2588-2603.
46. Sun L, Tran N, Liang C Hubbard S, Tang F. Identification of substituted 3-[(4,5,6,7-tetrahydro-1H-indol-2-yl)methylene]-1,3-dihydroindol-2-ones as growth factor receptor inhibitors for VEGF-R2 (Flk-1/KDR), FGF-R1, and PDGF-Rbeta tyrosine kinases. J Med Chem. 2000; 43: 2655-2663.
47. Zang X-P, Lerner M R, Dunn S T, Brackett D J, Pento J T. Antisense KGFR oligonucleotide inhibition of KGF-induced motility in breast cancer cells. Anticancer Res. (In Press).

48. Tong G M, Rajah T T, Pento J T. The differential influence of EGF- and IGF-1 and TGF-β on the invasiveness of human breast cancer cells. In Vitro Cell Dev Biol, 36: 493-94 (2000).
49. Tong G M, Rajah T T, Zang X-P, Pento J T. Antiestrogen inhibition of EGR-mediated invasiveness of human breast cancer cells. In Vitro Cell Dev Biol, 37: 578-80 (2001).
50. Nguyen T T, Zang X-P J T Pento. Keratinocyte growth factor stimulates the migration and proliferation of breast cancer cells in a culture wounding model. Pharmacological Res., 46: 179-83 (2002).
51. Zang X-P, Nguyen, T T Pento J T. Specific and non-specific KGF inhibition of KGF-induced breast cancer cell motility. Anticancer Res, 22: 2539-46 (2002).
52. Sledge G W, Qulali M, Goulet R, Bone E A, Fife R. Effect of MMP inhibitor batimastat on breast cancer regrowth and metastasis in athymic mice. J Natl Cancer Inst. 87:1545-1550 (1995).
53. Price J E. Metastasis from human breast cancer cell lines. Breast Cancer Res Treat. 39:93-102 (1996).

The invention claimed is:

1. A compound of formula II:

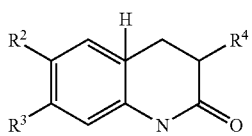

wherein $R^4$ is a substituted phenyl; wherein the phenyl has at least one substituent selected from the group consisting of sulfonamide, para-hydroxy, meta-ethoxy, meta-propoxy and meta-butoxy;
$R^2$ and $R^3$ are selected from the group consisting of H, ester, alkoxy, hydroxyl, and sulfonamide;
and pharmaceutically acceptable salts and esters thereof.

2. The compound of claim 1 wherein the compound is a keratinocyte growth factor receptor-tyrosine specific kinase (KGFR-TK) inhibitor.

3. A compound of formula III:

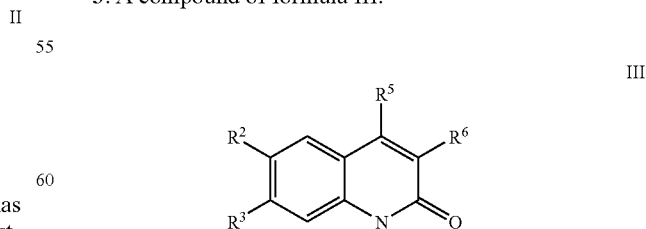

wherein $R^5$ is H and $R^6$ is substituted phenyl, wherein the substituted phenyl has at least one substituent selected from the group consisting of hydroxy, sulfonamide, and —$O(CH_2)_nOH$, wherein n is 1-4

R² is selected from the group consisting of H, amino, ester, carboxylic acid, alkoxy, hydroxyl, and sulfonamide;

R³ is selected from the group consisting of amino, carboxylic acid, alkoxy, and sulfonamide;

and pharmaceutically acceptable salts thereof.

4. The compound of claim 3 wherein R⁵ and R⁶ form a heteroaryl ring.

5. The compound of claim 4 wherein the heteroaryl ring is fused to another aromatic ring.

6. The compound of claim 5 wherein R⁵ and R⁶ form a furyl ring, wherein the furyl ring is fused to a benzene ring.

7. The compound of claim 3 wherein the compound is a keratinocyte growth factor receptor-tyrosine specific kinase (KGFR-TK) inhibitor.

8. A compound of the formula:

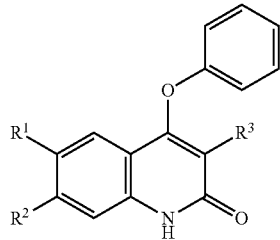

wherein R¹ is selected from the group consisting of amino, amide, ester, carboxylic acid, alkoxy, hydroxyl, and sulfonamide;

wherein R² is selected from the group consisting of H, amino, amide, ester, carboxylic acid, alkyl, alkoxy, hydroxyl, and sulfonamide;

wherein R³ is selected from the group consisting of H, phenyl, substituted aromatic, and phenoxy; wherein the substituted aromatic has at least one substituent selected from the group consisting of alkyl, hydroxy, alkoxy, sulfonamide, and O(CH₂)ₙOH, wherein n is 1-4; and pharmaceutically acceptable salts and esters thereof.

9. The compound of claim 8, wherein R¹ is selected from the group consisting of amide, ester, carboxylic acid, alkoxy, and hydroxyl; and wherein R² and R³ are H.

10. The compound of claim 8, wherein R¹ is carboxyl, R² is H, and R³ is H.

11. The compound of claim 8, wherein R¹ is hydroxyl, R² is H, and R³ is H.

* * * * *

SEQUENCE LISTING

<160> NUMBER OF SEQ ID NOS: 4

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Asp Ile Asn Arg Val Pro Glu Glu Gln Met Thr Phe
 1               5                  10

<210> SEQ ID NO 2
<211> LENGTH: 288
<212> TYPE: PRT
<213> ORGANISM: Homo sapiens

<400> SEQUENCE: 2

Leu Thr Leu Gly Lys Pro Leu Gly Glu Gly Cys Phe Gly Gln Val Val
 1               5                  10                  15

Met Ala Glu Ala Val Gly Ile Asp Lys Asp Lys Pro Lys Glu Ala Val
                20                  25                  30

Thr Val Ala Val Lys Met Leu Lys Asp Asp Ala Thr Glu Lys Asp Leu
            35                  40                  45

Ser Asp Leu Val Ser Glu Met Glu Met Met Lys Met Ile Gly Lys His
        50                  55                  60

Lys Asn Ile Ile Asn Leu Leu Gly Ala Cys Thr Gln Asp Gly Pro Leu
 65                  70                  75                  80

Tyr Val Ile Val Glu Tyr Ala Ser Lys Gly Asn Leu Arg Glu Tyr Leu
                 85                  90                  95

Arg Ala Arg Arg Pro Pro Gly Met Glu Tyr Ser Tyr Asp Ile Asn Arg
            100                 105                 110

Val Pro Glu Glu Gln Met Thr Phe Lys Asp Leu Val Ser Cys Thr Tyr
        115                 120                 125

Gln Leu Ala Arg Gly Met Glu Tyr Leu Ala Ser Gln Lys Cys Ile His
    130                 135                 140

Arg Asp Leu Ala Ala Arg Asn Val Leu Val Thr Glu Asn Asn Val Met
145                 150                 155                 160

Lys Ile Ala Asp Phe Gly Leu Ala Arg Asp Ile Asn Asn Ile Asp Tyr
                165                 170                 175

Tyr Lys Lys Thr Thr Asn Gly Arg Leu Pro Val Lys Trp Met Ala Pro
            180                 185                 190

Glu Ala Leu Phe Asp Arg Val Tyr Thr His Gln Ser Asp Val Trp Ser
        195                 200                 205

Phe Gly Val Leu Met Trp Glu Ile Phe Thr Leu Gly Gly Ser Pro Tyr
    210                 215                 220

Pro Gly Ile Pro Val Glu Glu Leu Phe Lys Leu Leu Lys Glu Gly His
225                 230                 235                 240

Arg Met Asp Lys Pro Ala Asn Cys Thr Asn Glu Leu Tyr Met Met Met
            245                 250                 255

Arg Asp Cys Trp His Ala Val Pro Ser Gln Arg Pro Thr Phe Lys Gln
            260                 265                 270

Leu Val Glu Asp Leu Asp Arg Ile Leu Thr Leu Thr Thr Asn Glu Glu
        275                 280                 285

<210> SEQ ID NO 3
<211> LENGTH: 288
<212> TYPE: PRT
<213> ORGANISM: Mus musculus

<400> SEQUENCE: 3

Leu Thr Leu Gly Lys Pro Leu Gly Glu Gly Cys Phe Gly Gln Val Val
1               5                   10                  15

Met Ala Glu Ala Val Gly Ile Asp Lys Asp Lys Pro Lys Glu Ala Val
            20                  25                  30

Thr Val Ala Val Lys Met Leu Lys Asp Asp Ala Thr Glu Lys Asp Leu
        35                  40                  45

Ser Asp Leu Val Ser Glu Met Glu Met Met Lys Met Ile Gly Lys His
    50                  55                  60

Lys Asn Ile Ile Asn Leu Leu Gly Ala Cys Thr Gln Asp Gly Pro Leu
65                  70                  75                  80

Tyr Val Ile Val Glu Tyr Ala Ser Lys Gly Asn Leu Arg Glu Tyr Leu
                85                  90                  95

Arg Ala Arg Arg Pro Pro Gly Met Glu Tyr Ser Tyr Asp Ile Asn Arg
            100                 105                 110

Val Pro Glu Glu Gln Met Thr Phe Lys Asp Leu Val Ser Cys Thr Tyr
        115                 120                 125

Gln Leu Ala Arg Gly Met Glu Tyr Leu Ala Ser Gln Lys Cys Ile His
    130                 135                 140

Arg Asp Leu Ala Ala Arg Asn Val Leu Val Thr Glu Asn Asn Val Met
145                 150                 155                 160

Lys Ile Ala Asp Phe Gly Leu Ala Arg Asp Ile Asn Asn Ile Asp Tyr
                165                 170                 175

Tyr Lys Lys Thr Thr Asn Gly Arg Leu Pro Val Lys Trp Met Ala Pro
            180                 185                 190

Glu Ala Leu Phe Asp Arg Val Tyr Thr His Gln Ser Asp Val Trp Ser
        195                 200                 205

Phe Gly Val Leu Met Trp Glu Ile Phe Thr Leu Gly Gly Ser Pro Tyr
    210                 215                 220

Pro Gly Ile Pro Val Glu Glu Leu Phe Lys Leu Leu Lys Glu Gly His
225                 230                 235                 240

Arg Met Asp Lys Pro Thr Asn Cys Thr Asn Glu Leu Tyr Met Met Met
            245                 250                 255

Arg Asp Cys Trp His Ala Val Pro Ser Gln Arg Pro Thr Phe Lys Gln
            260                 265                 270

Leu Val Glu Asp Leu Asp Arg Ile Leu Thr Leu Thr Thr Asn Glu Glu
        275                 280                 285

<210> SEQ ID NO 4
<211> LENGTH: 288
<212> TYPE: PRT
<213> ORGANISM: Homo sapiens

```
<400> SEQUENCE: 4

Leu Val Leu Gly Lys Pro Leu Gly Glu Gly Ala Phe Gly Gln Val Val
  1               5                  10                  15

Leu Ala Glu Ala Ile Gly Leu Asp Lys Asp Lys Pro Asn Arg Val Thr
                 20                  25                  30

Lys Val Ala Val Lys Met Leu Lys Ser Asp Ala Thr Glu Lys Asp Leu
             35                  40                  45

Ser Asp Leu Ile Ser Glu Met Glu Met Met Lys Met Ile Gly Lys His
         50                  55                  60

Lys Asn Ile Ile Asn Leu Leu Gly Ala Cys Thr Gln Asp Gly Pro Leu
 65                  70                  75                  80

Tyr Val Ile Val Glu Tyr Ala Ser Lys Gly Asn Leu Arg Glu Tyr Leu
                 85                  90                  95

Gln Ala Arg Arg Pro Pro Gly Leu Glu Tyr Ser Tyr Asn Pro Ser His
                100                 105                 110

Asn Pro Glu Glu Gln Leu Ser Ser Lys Asp Leu Val Ser Cys Ala Tyr
            115                 120                 125

Gln Val Ala Arg Gly Met Glu Tyr Leu Ala Ser Lys Lys Cys Ile His
            130                 135                 140

Arg Asp Leu Ala Ala Arg Asn Val Leu Val Thr Glu Asp Asn Val Met
145                 150                 155                 160

Lys Ile Ala Asp Phe Gly Leu Ala Arg Asp Ile His His Ile Asp Tyr
                165                 170                 175

Tyr Lys Lys Thr Thr Asn Gly Arg Leu Pro Val Lys Trp Met Ala Pro
            180                 185                 190

Glu Ala Leu Phe Asp Arg Ile Tyr Thr His Gln Ser Asp Val Trp Ser
            195                 200                 205

Phe Gly Val Leu Leu Trp Glu Ile Phe Thr Leu Gly Gly Ser Pro Tyr
    210                 215                 220

Pro Gly Val Pro Val Glu Glu Leu Phe Lys Leu Leu Lys Glu Gly His
225                 230                 235                 240

Arg Met Asp Lys Pro Ser Asn Cys Thr Asn Glu Leu Tyr Met Met Met
                245                 250                 255

Arg Asp Cys Trp His Ala Val Pro Ser Gln Arg Pro Thr Phe Lys Gln
            260                 265                 270

Leu Val Glu Asp Leu Asp Arg Ile Val Ala Leu Thr Ser Asn Gln Glu
            275                 280                 285
```